US009302896B2

(12) United States Patent
Drenguis et al.

(10) Patent No.: US 9,302,896 B2
(45) Date of Patent: Apr. 5, 2016

(54) METHOD OF STERILIZING BOTTLES WITH ELECTRON RADIATION AND A STERILIZING ARRANGEMENT THEREFOR

(75) Inventors: Alfred Drenguis, Börnsen (DE); Volker Till, Hofheim am Taunus (DE)

(73) Assignee: KHS GmbH, Dortmund (DE)

( * ) Notice: Subject to any disclaimer, the term of this patent is extended or adjusted under 35 U.S.C. 154(b) by 753 days.

(21) Appl. No.: 12/847,538

(22) Filed: Jul. 30, 2010

(65) Prior Publication Data

US 2011/0016829 A1    Jan. 27, 2011

Related U.S. Application Data

(63) Continuation-in-part of application No. PCT/EP2009/000399, filed on Jan. 23, 2009.

(30) Foreign Application Priority Data

Feb. 1, 2008  (DE) .......................... 10 2008 007 428

(51) Int. Cl.
*B65B 55/04* (2006.01)
*B67C 7/00* (2006.01)
*A61L 2/08* (2006.01)
*B65B 55/08* (2006.01)
*B67B 3/20* (2006.01)

(52) U.S. Cl.
CPC .............. *B67C 7/0073* (2013.01); *A61L 2/087* (2013.01); *B65B 55/08* (2013.01); *B67B 3/2033* (2013.01); *A61L 2202/23* (2013.01); *B67B 2201/08* (2013.01)

(58) Field of Classification Search
CPC ...... B65B 55/08; A61L 2/087; A61L 2202/23; B67C 7/0073; B67C 3/2642; B67B 3/2033
USPC ................... 53/426, 425, 467, 471, 167, 485; 422/22; 250/395
See application file for complete search history.

(56) References Cited

U.S. PATENT DOCUMENTS 2,384,778 A    9/1945  Whitman
6,368,554 B1   4/2002  Wajsfelner et al.

(Continued)

FOREIGN PATENT DOCUMENTS

DE    198 82 252 T1   5/2000
EP      1 561 722 A   8/2005

(Continued)

OTHER PUBLICATIONS

International Search Report PCT/EP2009/000399.
German Office Action 10 2008 007 428.4-27.

*Primary Examiner* — Robert Long
*Assistant Examiner* — Xavier A Madison
(74) *Attorney, Agent, or Firm* — Nils H. Ljungman & Associates

(57) ABSTRACT

A method and apparatus for sterilizing containers, such as cans, bottles, or similar containers. The method involves relatively moving a container and an elongated electron radiation treatment member with respect to one another, such that the treatment member is located in the container. The treatment member is used to treat the entire inside surface of the container with identical or essentially identical radiation power, and then is removed from the container.

9 Claims, 6 Drawing Sheets

(56) References Cited

U.S. PATENT DOCUMENTS

| | | |
|---|---|---|
| 2005/0158218 A1 | 7/2005 | Dumargue et al. |
| 2005/0188651 A1 | 9/2005 | Clusserath |
| 2006/0011263 A1* | 1/2006 | Till .............................. 141/147 |
| 2007/0237672 A1 | 10/2007 | Colato et al. |
| 2007/0283667 A1* | 12/2007 | Kristiansson et al. .......... 53/426 |
| 2008/0073549 A1* | 3/2008 | Avnery ........................ 250/397 |
| 2008/0317624 A1* | 12/2008 | Gueguen et al. ................ 422/26 |
| 2009/0013646 A1* | 1/2009 | Mastio et al. .................. 53/425 |

FOREIGN PATENT DOCUMENTS

| | | |
|---|---|---|
| EP | 1 736 174 A1 | 12/2006 |
| FR | 28 65 135 A1 | 7/2005 |
| JP | S63281936 A | 11/1988 |
| WO | WO 2005/108278 A | 11/2005 |
| WO | WO 2007/095205 A2 | 8/2007 |
| WO | WO 2007/145 561 A1 | 12/2007 |
| WO | WO 2008/070 956 A1 | 6/2008 |
| WO | WO 2008/073 015 A1 | 6/2008 |

* cited by examiner

METHOD OF STERILIZING BOTTLES WITH ELECTRON RADIATION AND A STERILIZING ARRANGEMENT THEREFOR

CONTINUING APPLICATION DATA

This application is a Continuation-In-Part application of International Patent Application No. PCT/EP2009/000399, filed on Jan. 23, 2009, which claims priority from Federal Republic of Germany Patent Application No. 10 2008 007 428.4, filed on Feb. 1, 2008. International Patent Application No. PCT/EP2009/000399 was pending as of the filing date of this application. The United States was an elected state in International Patent Application No. PCT/EP2009/000399.

BACKGROUND

1. Technical Field

The present application related to a method and apparatus for treating packaging and an installation for filling and closing packaging, including an apparatus for treating packaging.

2. Background Information

Background information is for informational purposes only and does not necessarily admit that subsequently mentioned information and publications are prior art.

A beverage bottling plant for filling bottles with a liquid beverage filling material can possibly comprise a beverage filling machine, which is often a rotary filling machine, with a plurality of beverage filling positions, each beverage filling position having a beverage filling device for filling bottles with liquid beverage filling material. The filling devices may have an apparatus designed to introduce a predetermined volume of liquid beverage filling material into the interior of bottles to a substantially predetermined level of liquid beverage filling material.

Some beverage bottling plants may possibly comprise filling arrangements that receive a liquid beverage material from a toroidal or annular vessel, in which a supply of liquid beverage material is stored under pressure by a gas. The toroidal vessel may also be connected to at least one external reservoir or supply of liquid beverage material by a conduit or supply line. In some circumstances it may even be possible that a beverage bottling plant has two external supply reservoirs, each of which may be configured to store either the same liquid beverage product or different products. These reservoirs could possibly be connected to the toroidal or annular vessel by corresponding supply lines, conduits, or other arrangements. It is also possible that the external supply reservoirs could be in the form of simple storage tanks, or in the form of liquid beverage product mixers.

A wide variety of types of filling elements are used in filling machines in beverage bottling or container filling plants for dispensing a liquid product into bottles, cans or similar containers, including but not limited to filling processes that are carried out under counterpressure for the bottling of carbonated beverages. The apparatus designed to introduce a predetermined flow of liquid beverage filling material further comprises an apparatus that is designed to terminate the filling of the beverage bottles upon the liquid beverage filling material reaching the predetermined level in bottles. There may also be provided a conveyer arrangement that is designed to move bottles, for example, from an inspecting machine to the filling machine.

After a filling process has been completed, the filled beverage bottles are transported or conveyed to a closing machine, which is often a rotary closing machine. A revolving or rotary machine comprises a rotor, which revolves around a central, vertical machine axis. There may further be provided a conveyer arrangement configured to transfer filled bottles from the filling machine to the closing station. A transporting or conveying arrangement can utilize transport star wheels as well as linear conveyors. A closing machine closes bottles by applying a closure, such as a screw-top cap or a bottle cork, to a corresponding bottle mouth. Closed bottles are then usually conveyed to an information adding arrangement, wherein information, such as a product name or a manufacturer's information or logo, is applied to a bottle. A closing station and information adding arrangement may be connected by a corresponding conveyer arrangement. Bottles are then sorted and packaged for shipment out of the plant.

Many beverage bottling plants may also possibly comprise a rinsing arrangement or rinsing station to which new, non-return and/or even return bottles are fed, prior to being filled, by a conveyer arrangement, which can be a linear conveyor or a combination of a linear conveyor and a starwheel. Downstream of the rinsing arrangement or rinsing station, in the direction of travel, rinsed bottles are then transported to the beverage filling machine by a second conveyer arrangement that is formed, for example, by one or more starwheels that introduce bottles into the beverage filling machine.

It is a further possibility that a beverage bottling plant for filling bottles with a liquid beverage filling material can be controlled by a central control arrangement, which could be, for example, a computerized control system that monitors and controls the operation of the various stations and mechanisms of the beverage bottling plant.

In many areas, for example also in the pharmaceutical, foodstuffs or beverage industry, it is necessary and/or may be desired to package products or to fill them into containers in a sterile or germ-free manner and then to close said containers in a germ-free manner. In this case, the principle of sterilizing the packaging used by means of heating it is also known (hot sterilization). Said hot sterilization, however, is not possible or is not desirable in many cases, for example on account of the high energy consumption or on account of the danger of destroying or damaging the container, for example if made of plastics materials (e.g. PET).

To avoid, restrict, and/or minimize hot sterilization, among other things, a method is known for sterilizing the insides of containers using electron radiation, i.e. for electron sterilization or electron disinfection. In the case of the known method, the treatment of the containers is effected by way of an electron beam, which has a beam intensity or output in the order of one hundred to two hundred fifty kiloelectron volt, such that the electron beam, for sterilization of the interior, is introduced into the respective container through the container opening. During the treatment, the radiation source or the treatment head formed by said radiation source is situated outside the respective container and above the container mouth of the container that is arranged standing upright during the treatment. In this case, the distance between the treatment head or the radiation source and the inside surface of the container to be treated is relatively large, i.e. the electron radiation has to or should cover a relatively large path before it contacts the inside surface of the container to be treated, and, in addition, for example in the case of containers that are realized as bottles, the radiation cross section determined by the cross section of the container or bottle mouth is relatively small, such that to achieve the necessary and/or desired sterility or the dose of radiation ensuring said sterility, a high output of electron radiation and/or a relative long treatment duration are necessary and/or desired.

A sterilization of the interior of containers by way of electron radiation through the container wall is not possible as the range of said beams, at least with reasonable intensities or outputs of the electron beams, is very small in the material conventionally used for packaging means.

To avoid, restrict, and/or minimize damaging the material of the container, for example also in the case of containers made of plastics material where high radiation doses of electron radiation result in the material becoming brittle, it is necessary and/or desired to have an expensive system of diaphragms which essentially ensures or promotes that the electron radiation output by the treatment head is actually introduced exclusively or substantially exclusively into the interior of each container being treated and does not contact regions of the container wall surrounding the container mouth.

OBJECT OR OBJECTS

It is an object of the present application to provide a method for electron sterilization or electron disinfection, which avoids, restricts, and/or minimizes the aforementioned disadvantages and which, with reduced radiation intensity and consequently reduced energy consumption and reduced radiation exposure of the packaging means, essentially ensures or promotes the necessary and/or desired sterility.

SUMMARY

This object may be achieved by a method for sterilizing packaging means, such as, for example, cans, bottles or similar containers, by treating the inside surface of the packaging means with electron radiation from at least one treatment head. The treatment head for the treatment is placed in the respective packaging means or in the interior of the packaging means through a packaging means opening.

Another object of the present application may be a device for treating packaging means, in one possible embodiment packaging means realized as hollow bodies, such as, for example, cans, bottles or similar containers, said device having at least one treatment station with at least one treatment head with an electron beam source for electron sterilization or electron disinfection. For the electron sterilization or electron disinfection of the respective interior of the packaging means, the at least one treatment station is realized for placing the at least one treatment head in the packaging means during the treatment and for removing the at least one treatment head out of the packaging means after the treatment. Another object of the present application may be a device for treating packaging means in the form of closures for cans, bottles or similar containers, said device having at least one treatment station with at least one treatment head with an electron beam source for electron sterilization or electron disinfection. The at least one treatment head is provided for the electron sterilization or electron disinfection of at least the respective inside of the closure directly prior to the closing of a container. Another object may be an installation for filling and closing packaging means, such as, for example, cans, bottles or similar containers, said installation having a packing or filling machine located in a sterile or clean room and a closing machine located in the sterile or clean room. In addition, a device for the electron beam sterilization or electron beam disinfection of the packaging means or of the respective interior of the packaging means prior to it being conveyed further to the packing or filling machine is provided in the sterile or clean room.

Packaging means in the terms of the present application are, in one possible embodiment, containers, such as cans and bottles and their closures, in one possible embodiment also using packaging means produced from or comprising plastics material.

Electron radiation in the terms of the present application is first and foremost the electron radiation delivered by at least one electrically driven electron beam source. However, electron radiation, in terms of the present application, is also the radiation delivered by a beta radiation source.

In the case of the present application, the internal sterilization of the packaging means is also effected, in one possible embodiment, by means of impinging the interior surfaces of the packaging means with electron radiation (beta radiation). The distinctive feature in this case is that the respective treatment head or the electron beam source formed by said treatment head is introduced through the opening of the respective packaging means for internal sterilization, such that, at reduced radiation intensity of the electron radiation delivered by the treatment head, sterilization at a sufficiently high dose is possible.

Further developments, embodiments and application possibilities of the present application are produced from the following description of possible embodiments and from the Figures. In this case, the described and/or graphically represented features, individually or in arbitrary combination, are, in principle, objects of the present application.

The present application relates to a method according to a method for sterilizing packaging means, such as, for example, cans, bottles or similar containers, by treating the inside surface of the packaging means with electron radiation from at least one treatment head. The present application also relates to a device for treating packaging means, in one possible embodiment packaging means realized as hollow bodies, such as, for example, cans, bottles or similar containers. The device may comprise at least one treatment station with at least one treatment head with an electron beam source for electron sterilization or electron disinfection. The present application may also relate to a device for treating packaging means in the form of closures for cans, bottles or similar containers. The device may comprise at least one treatment station with at least one treatment head with an electron beam source for electron sterilization or electron disinfection. The present application may also relate to an installation for filling and closing packaging means, such as, for example, cans, bottles or similar containers. The installation may comprise a packing or filling machine located in a sterile or clean room and a closing machine located in the sterile or clean room.

The above-discussed embodiments of the present invention will be described further herein below. When the word "invention" or "embodiment of the invention" is used in this specification, the word "invention" or "embodiment of the invention" includes "inventions" or "embodiments of the invention", that is the plural of "invention" or "embodiment of the invention". By stating "invention" or "embodiment of the invention", the Applicant does not in any way admit that the present application does not include more than one patentably and non-obviously distinct invention, and maintains that this application may include more than one patentably and non-obviously distinct invention. The Applicant hereby asserts that the disclosure of this application may include more than one invention, and, in the event that there is more than one invention, that these inventions may be patentable and non-obvious one with respect to the other.

BRIEF DESCRIPTION OF THE DRAWINGS

The present application is explained below by way of the Figures of a possible embodiment, in which, in detail.

DESCRIPTION OF EMBODIMENT OR EMBODIMENTS

Figure 1:
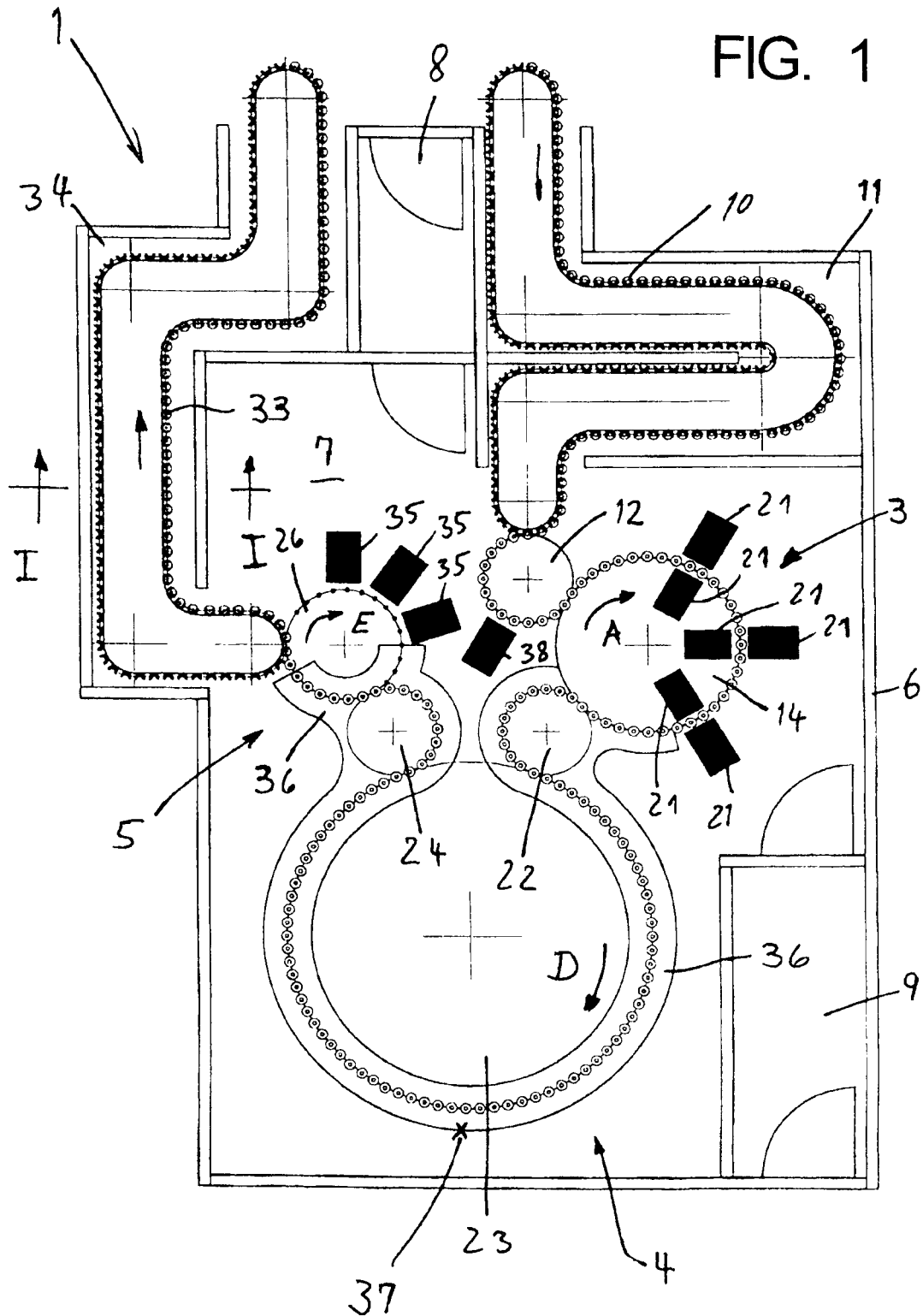
FIG. 1 shows a simplified representation and top view of an installation for the sterile filling of a liquid product into containers that are realized as bottles.

The installation given the general reference 1 in the Figures serves for the sterile or aseptic, for example cold aseptic filling of a liquid product into bottles 2, which are realized as PET bottles in the embodiment represented.

The installation 1 essentially comprises a sterilizer 3, a filling machine 4 and a closing machine 5, which are each realized as machines of the rotating type and are accommodated in a sterile or clean room 7 that is closed relative to the surrounding area by means of an enclosure 6, said sterile or clean room being accessible by means of two staff locks 8 and 9, for example for the purposes of cleaning, maintenance and/repairs.

The bottles 2 to be filled are supplied to the installation 1 by means of a conveyor 10 and an entry lock 11 and by way of said conveyor 10, formed essentially by an endlessly driven conveyor belt, reach the sterile or clean room 7, where, via a transport star 12 driven in a rotating manner about a vertical or substantially vertical axis, they are transferred in each case singly one after the other to a treatment station 13, which is provided together with a plurality of identical-type treatment stations 13 at the periphery of a rotor 14 of the sterilizer 3, said rotor being driveable in a rotating (arrow A) manner about a vertical or substantially vertical machine axis (MA1).

The treatment stations 13, which are located at uniform angular spacings about the vertical or substantially vertical machine axis of the rotor 14, comprise, in the embodiment represented, in each case essentially a treatment head 15, which, among other things, has a device for creating electron radiation (electron beam source) at sufficiently high energy, for instance in the order of one hundred through one hundred fifty kiloelectron volts, as well as container support 16. When the electron beam source is activated, the electron radiation (beta radiation) is output in a radial manner and also in an axial manner from the treatment head 15 in a uniform or substantially uniform radiation characteristic that surrounds the axis of the treatment head 15.

Figure 2:
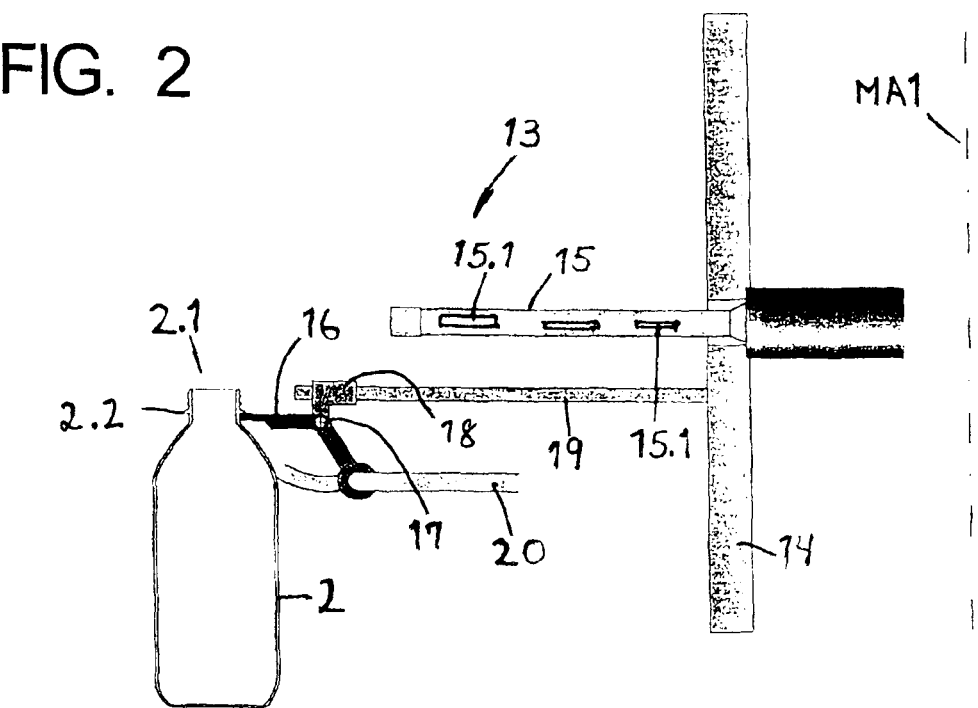
FIGS. 2 through 4 show one of the treatment stations of a sterilizer of the installation in FIG. 1 in various operating states.
Figure 3:
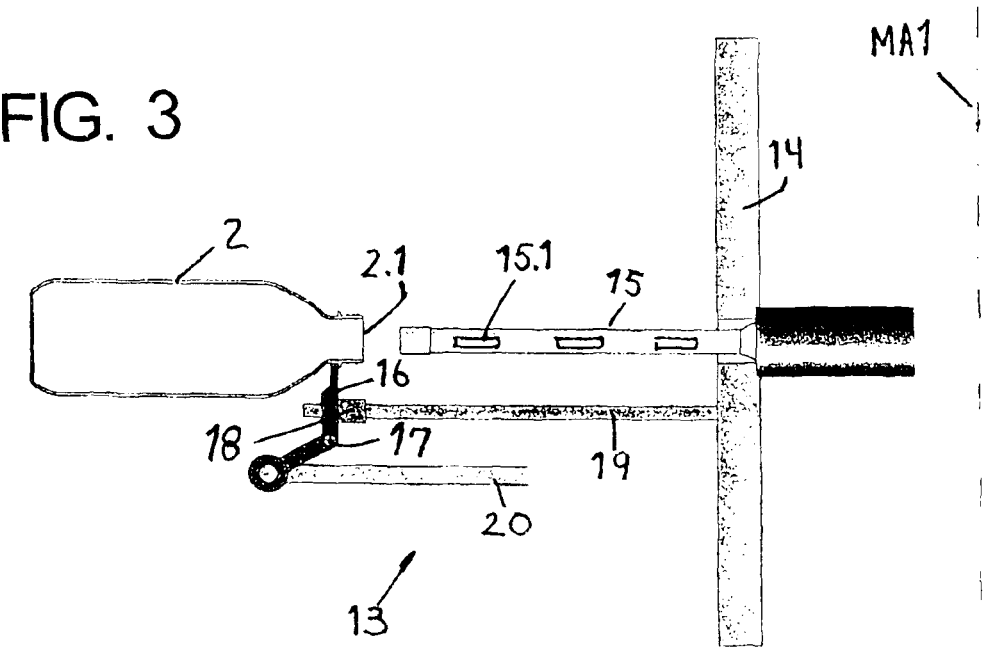

The individual treatment heads 15 are each provided on the rotor 14 such that they stand out from said rotor, oriented with their axes radially or substantially radially to the machine axis MA1 of the rotor 14. The container supports 16 are each realized for holding the bottle 2 at its bottle neck or at a neck or mouth flange 2.2 in the region of the bottle mouth 2.1 and are pivotable in a controlled manner about horizontal or substantially horizontal axes tangentially or substantially tangentially to the movement of rotation of the rotor 14 as well as moveable radially in a controlled manner with reference to the vertical or substantially vertical axis of rotation MA1 of the rotor 14. To this end, the container supports 16 are each pivotally mounted at 17 on a carriage 18, which is located so as to be displaceable at a radial guide 19. The control of the pivotal movement (double arrow B) and the radial movement (double arrow C) is effected via a linkage 20, for example in a cam-controlled manner synchronously or substantially synchronously with the movement of rotation of the rotor 14, such that each bottle 2 accommodated by a treatment station 13 or by the container carrier 16 at that location is held in a suspended manner on said container carrier, oriented with the bottle axis in the vertical or substantially vertical direction and with the bottle mouth 2.1 pointing upwards (FIG. 2). With the rotor 14 rotating about the vertical or substantially vertical machine axis, the respective bottle 2, located at a treatment station 13, is then pivoted with the container carrier 16 such that its bottle axis is located oriented in the horizontal or substantially horizontal direction radially relative to the machine axis MA1 and on the identical axis or substantially on the identical axis as the axis of the rod-shaped treatment head 15. The respective bottle 2 is then situated initially still at a radial spacing from the machine axis MA1 which is greater than the spacing between the free end of the treatment head 15 and said axis, the respective bottle 2 facing the treatment head 15 with its bottle mouth 2.1 (FIG. 3).

Figure 4:
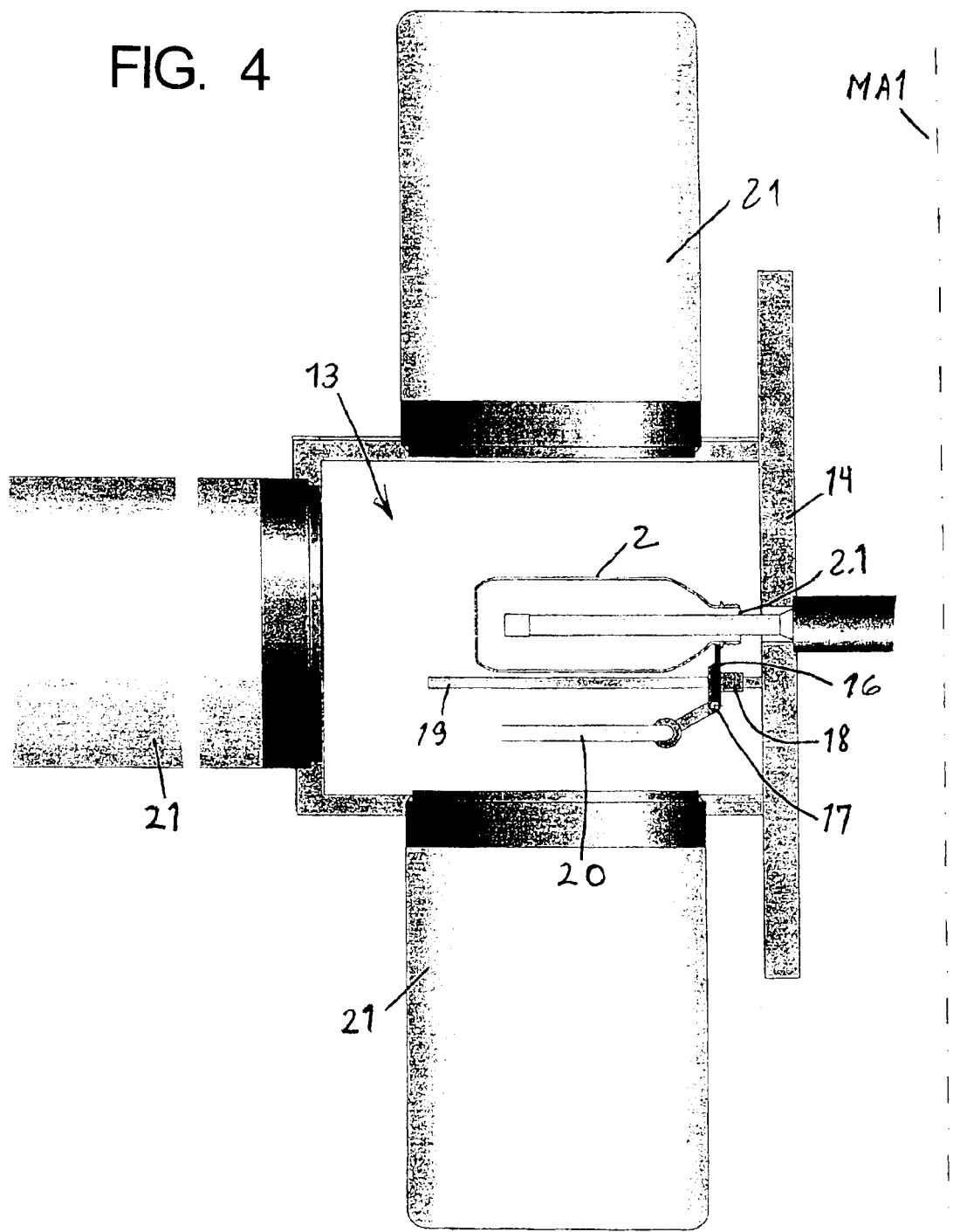

At another angular region of the rotary movement of the rotor 14, the treatment head 15 is then placed in the bottle 2, by moving the carriage 18 and consequently the bottle 2 radially inwards with reference to the machine axis MA1. As soon as said state represented in FIG. 4 has been reached, by activating the electron beam source the inner surfaces of the bottle 2 are treated, via the treatment head 15 introduced in the bottle 2, for electron sterilization or electron disinfection, i.e. for killing off any germs that may be present by way of electron radiation, for a sufficient length of time or at a sufficient dose of radiation, for example in the order of nine through sixty kiloGrays (0.9 through six milliradians). The intensity of the electron radiation, in this case, is selected such that the electrons achieve an insertion depth of 0.01 millimeter through 0.3 millimeter into the material of the bottle 2. By introducing the treatment heads 15 into the bottles 2 and by means of the rod-shaped embodiment of the treatment heads 15 such that, once they have been introduced, they each extend over the larger part of the bottle height, it is possible, at relatively low intensity of electron radiation, to achieve the dose of radiation necessary and/or desired for the required and/or desired sterility, e.g. for a log 6 germ reduction, for example within the range of nine through sixty kiloGrays, thus saving energy and without any damage being caused to the material, in one possible embodiment even to the plastics material of the bottles 2, caused by the electron radiation.

During the treatment of the bottles 2 on the inside surfaces of the bottles by way of the radiation heads 15, the bottles are also treated on the outside surfaces by means of additional treatment heads 21, which, in their turn, essentially comprise an electron beam source and are provided in a plurality of groups, following one after the other in the direction of rotation A of the rotor 14, not being entrained with the rotor 14, on the path of movement of the treatment stations 13 and of the bottles 2 provided at said stations. Each group, in the embodiment represented, comprises three treatment heads 21, of which one treatment head 21 is located above the path of movement of the treatment stations 13 and consequently of the bottles 2 located on the treatment heads 15, one treatment head 21 is located below said path of movement and one treatment head 21 is located lying radially outside with reference to the path of movement, such that, when passing the groups of treatment heads 21, each bottle 2 is treated with electron or beta radiation over all or substantially all regions of its outside surface to achieve the necessary and/or desired germ reduction. The treatment heads 21 are also realized in each case for the delivery of electron radiation at an output of one hundred to one hundred fifty kiloelectron volts.

In one possible embodiment of the present application, the treatment heads 21 may be realized and/or configured to output electron radiation at less than one hundred kiloelectron volts. In yet another possible embodiment of the present application, the treatment heads 21 may be realized and/or configured to output electron radiation at more than one hundred fifty kiloelectron volts.

The output of the treatment heads 15 and 21 or their electron beam sources is/are designed such that at a maximum output of the installation 1, the bottles 2 are treated with a dose of radiation that is sufficient for the germ reduction targeted, for example within the range between nine and sixty kiloGrays.

In one possible embodiment of the present application, the dose of radiation outputted by the treatment heads 15 and 21 may be less than nine kiloGrays. In yet another possible embodiment of the present application, the dose of radiation outputted by the treatment heads 15 and 21 may be more than sixty kiloGrays.

In the case of one possible embodiment, the treatment heads 15 forming the respective electron beam source or the electron beam sources associated with said treatment heads are actively cooled, i.e. by using a cooling medium that is, for example, liquid or vaporous and/or gaseous.

In addition, the treatment heads 15 can be realized such that they also carry out a treatment of the bottle interiors by way of a gaseous and/or vaporous and/or liquid medium, for example $CO_2$, $N_2$ and/or sterile air. In addition, the treatment heads 15 can also be realized for removing or aspirating gaseous and/or vaporous constituents from the treated bottles 2, for example for aspirating active oxygen (ozone) that may possibly be created during the electron sterilization or electron disinfection.

After the treatment of the respective bottle 2 with the treatment head 15, said treatment head or the associated electron beam source is switched off and the bottle 2 is also moved back into the suspended initial position corresponding to FIG. 2 by means of the controlled displacement of the carriage 18 radially outwards and by pivoting back the container carrier 16, such that each sterilized bottle 2 can be transferred by means of a transport star 22, driven in a rotating manner about a vertical or substantially vertical axis, to a filling position of the filling machine 4, said filling position being provided with a plurality of identical-type filling positions at the periphery of a rotor 23 (arrow D) that is driven in a rotating manner about a vertical or substantially vertical axis and has an embodiment known to the person skilled in the art of filling machines.

Once filled with the liquid product, each bottle 2 is transferred via a transport star 24, driven in a rotating manner about a vertical or substantially vertical axis, to the closing machine 5 or to a closing position 25 at that location, which is provided together with a plurality of identical-type closing positions 25 at the periphery of a rotor 26 of the closing machine 5, said rotor being driven in a rotating manner about a vertical or substantially vertical machine axis M2. Each closing position 25 essentially comprises a closing tool 27 with a closing or tool head 28 and a container carrier 29 provided below the closing tool 27 on the rotor 26, which, in the embodiment represented, once again is realized for a suspended mounting of the bottles 2 at their bottle neck or at the neck or mouth flange 2.2 at that location.

Figure 5:
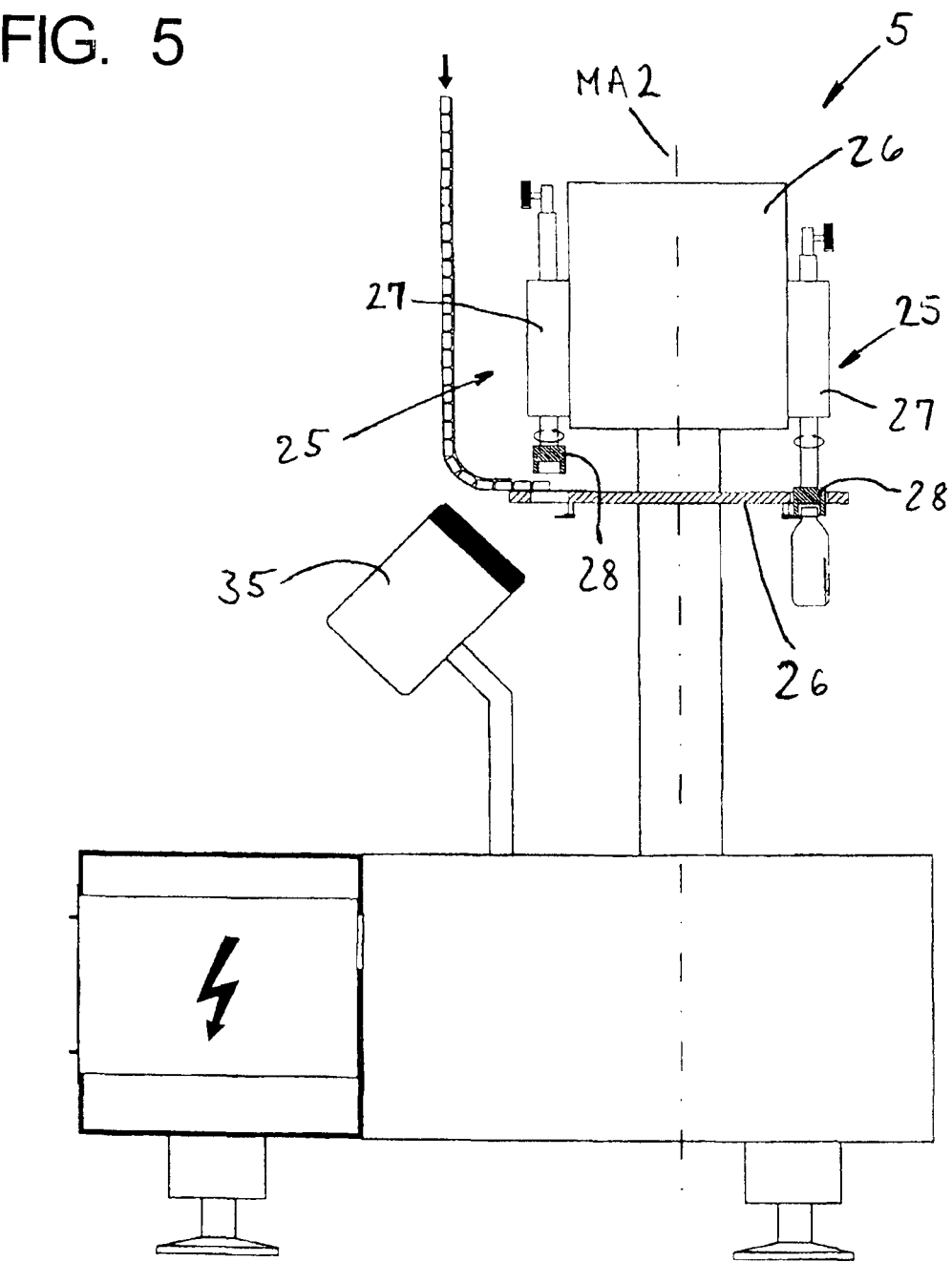
FIG. 5 shows a schematic representation and side view of a closing machine of the installation in FIG. 1, together with a treatment head for sterilizing the closures supplied to the closing machine.

Such a closing machine may be seen in FIG. 5 of the present application.

The closing machine 5 or its closing tools 27 are realized for processing screw-type closures, i.e. closures or covers that are securable by means of being screw-connected on threads at the bottle neck and for this reason have the design known to the person skilled in the art that is necessary and/or desired for processing such types of closures 30.

Figure 6:
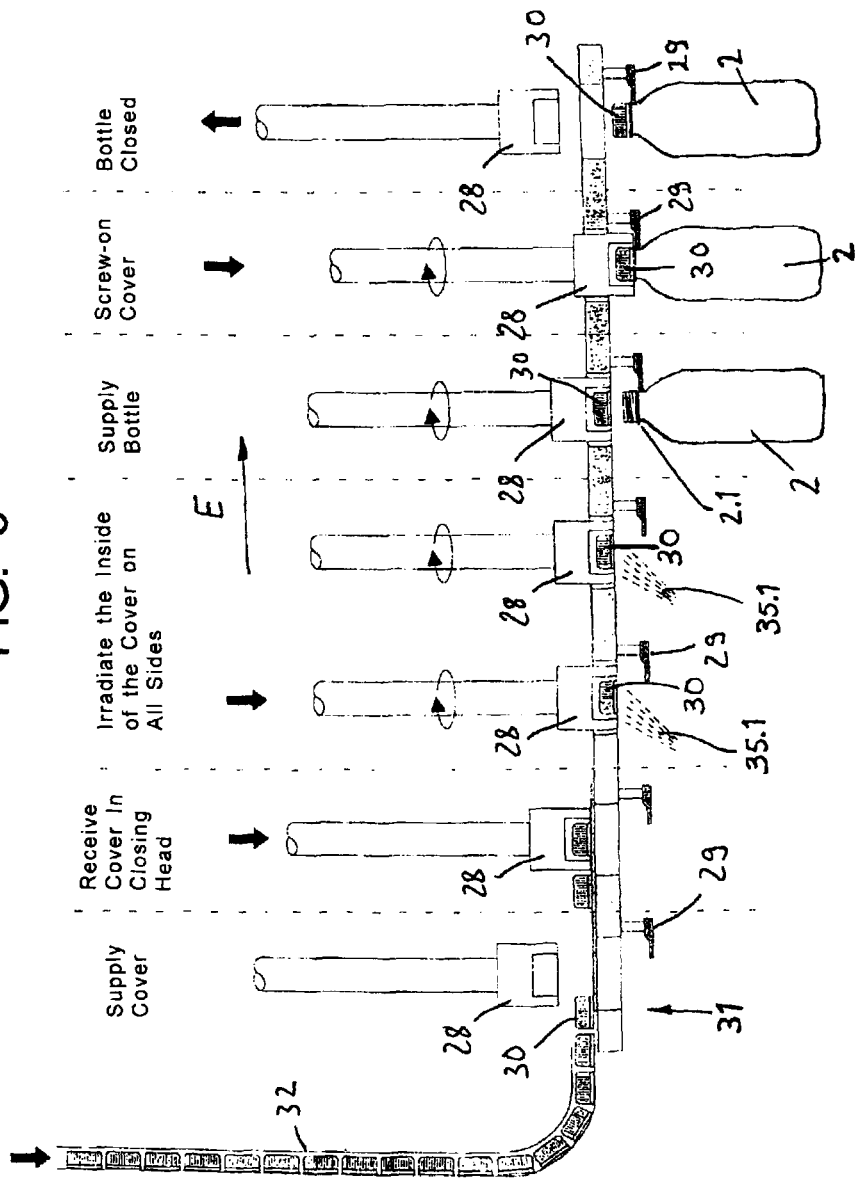
FIG. 6 shows a simplified representation of the time sequence when supplying, sterilizing and fitting the closures onto the bottles.
Figure 7:
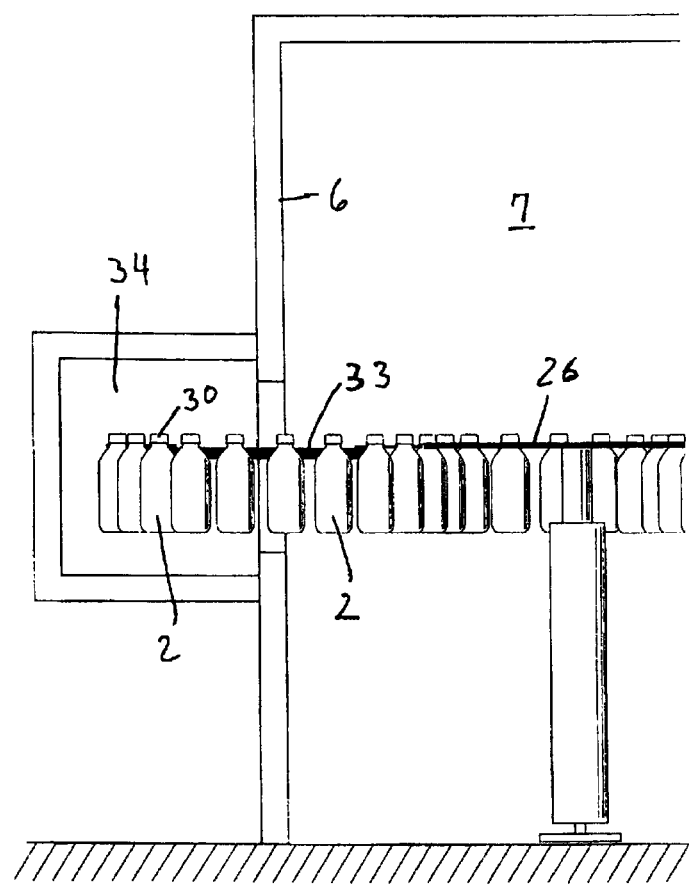
FIG. 7 shows a section corresponding to the line I-I in FIG. 1.

As can also be seen in one possible embodiment in FIG. 6, the closures 30 are supplied to the closing machine 5 or to a closure removal position 31 of said machine via a guiding means 32, then at the closure removal position, with the rotor rotating 26, are each taken over by a tool head 28, entrained with said tool head and finally fitted onto the bottle 2, at the relevant closing position 25, being held there in a suspended manner and secured to said bottle by means of being screw-connected. The bottles closed in this manner are transferred from the closing machine 5 to a conveyor 33, which is formed by an endlessly circulating conveyor belt, by means of which conveyor the filled and closed bottles 2 are moved out of the sterile or clean room 7 through an exit lock 34 and are supplied to another processing, for example a labeling machine, by means of an external conveyor (not represented).

The closing of the bottles 2 with the closures 30 is effected at the angular region of the movement of rotation (arrow E) of the rotor 26 between the transport star 24 and the conveyor 33. The distinctive feature of the closing machine 5 is that the closing heads 28, and in one possible embodiment also the closures 30 held at said closing heads, are treated several times with electron beams 35.1 (FIG. 6) on the inside of the closure, i.e. on all or substantially all surfaces that come into contact or could come into contact with the liquid, at the angular region of the rotary movement (E) of the rotor 26 between the closure removal position 31 and the fitting of the closures onto the bottles 2. For this purpose, in the direction of rotation of the rotor 26 following the closure removal position 31 in the embodiment represented, three treatment heads 35, which, in their turn, essentially comprise an electron beam source, are provided at the periphery of the rotor 26 and are not entrained by said rotor. The effective direction or radiation direction of the treatment heads 35 is directed in each case inclinedly from below onto the closing and tool heads 28 as well as onto the container supports 29. The output of the treatment heads 35 or their electron beam sources is designed such that, at maximum output of the installation 1, the closures 30 are treated with a dose of radiation that is sufficient for the targeted germ reduction within the range between nine and sixty kiloGrays.

It has already been described above that the bottles 2 are held in a suspended manner, at least at the inlet and outlet of the sterilizer 3, at the filling machine 4 and also at the closing machine 5 or at the closing stations 25 arranged at that location. The remaining transport elements, namely the conveyors 10 and 33 and the transport stars 12, 22 and 24 are also realized in each case for a suspended arrangement or mounting of the bottles 2 at their neck flange 2.2.

As indicated in FIG. 1 with the reference 36, the bottles 2 are moved at least at the outlet of the sterilizer 3 as far as the final closing operation, i.e. as far as the transfer to the conveyor 33, through a channel 36, which is defined by wall sections, sometimes also by wall sections rotating with the rotors 14, 23 and 26, on both sides and at the top and at the bottom and which is impinged upon by sterile air by means of at least one inlet 37, such that said sterile air flows through the channel 36 and emerges from the channel 36 at one end at the sterilizer 3 and at the other end at the closing machine 5, such that this may also provide essentially an extra guarantee or may promote against any new contamination of the sterilized bottles 2 prior to the closing operation, or may restrict and/or minimize contamination of the sterilized and/or treated bottles 2 prior to the closing operation.

The sterile or clean room 7 is also obviously also impinged upon with sterile air by means of additional inlets, such that the pressure in the sterile or clean air room 7 is somewhat higher than the atmospheric pressure and consequently an air flow preventing contamination of the sterile or clean room 7 is produced through the entry lock 11 and the exit lock 34 to the outside.

The treatment heads 21 and 35, in the case of the installation 1 described, are arranged in such a manner and aligned with regard to the beam direction of the electron radiation that such surface regions of the bottles 2 or closures 30, which, when passing a treatment head 21 or 35, are located in the "shadow" of operating elements, for example in the "shadow" of the container support 16 or of the closing or tool head 28, when passing an additional treatment head 21 or 25, are fully impinged upon with the electron radiation by way of said treatment head.

Each treatment head 15 essentially comprises a cylindrical housing, in which the electron beam source is located and which is provided on its outside surface and also at the free end with windows 15.1 (electron beam outlet windows), which are closed in each case by way of a thin wall of film made from material that is permeable to the electron radiation, for example titanium.

In an identical manner, the treatment heads 21 and 35, in each case, also comprise a housing that accommodates the electron beam source and has outlet windows for the electron radiation, said windows, in their turn, being closed by the film that is permeable to the electron radiation. To protect the film closing the electron beam outlet windows during maintenance and/or the cleaning of the installation 1, the treatment heads 15, 21 and 35 are coverable, at least at their surfaces that have said electron beam output windows, with protective covers.

As shown in FIG. 1, a further treatment head 38 with electron beam source is provided at the transport star 12 for the electron sterilization or electron disinfection of the outside surface of the bottles 2 that are moved passed.

The present application has been described above by way of possible embodiments. It is obvious that numerous modifications and conversions are possible without departing from the teaching concept underlying the present application.

The present application has been described above by way of the example of an installation for sterilizing, filling and closing bottles 2. The present application is obviously also suitable for application with other packaging means or containers, for example cans.

It has additionally been assumed above that to place the respective treatment head 15 in position, the bottle 2 or the corresponding container is moved relative to the treatment head 15. In principle, it is also possible to introduce the respective treatment head 15 or a treatment head corresponding to the function into the respective container and to move it back out of the container again after the treatment.

It has additionally been assumed above that in the case of a sterilizer 3 or in the case of a device for sterilizing using electron radiation or beta radiation, the electron beam source is a plurality of treatment heads 15. In principle, it is also possible to provide one electron beam source in common to all or substantially all the treatment stations 13 or also to a group of such stations.

It has additionally been assumed above that the rod-shaped treatment head 15 is oriented during the treatment with its axis horizontally or substantially horizontally and accordingly the placing in position of the treatment head in the container as well as the removing of the treatment head out of the container is effected by means of a relative movement between container or bottle and treatment head 15, said relative movement having at least one horizontal or substantially horizontal component. The relative movement between treatment head and container can also be carried out in another direction, for example in the vertical or substantially vertical direction, e.g. in the manner that the treatment head is positioned in the container by raising the container and/or by lowering the treatment head and is removed out of the container again by a movement in the reverse direction, i.e. by lowering the container and/or raising the treatment head.

Common to the embodiments of the present application is that, during the treatment of the respective container on its inside surface, the treatment head 15 is introduced through the container mouth into the interior of the container such that, at a reduced dose of radiation within the range of, for example, just nine through sixty kiloGrays, the disinfection is achieved with the targeted quality or at the targeted reduced germ rad without there being any danger, in one possible embodiment, of damaging the material of the container through an excessive dose of radiation.

The present application relates to a method and a device for sterilizing packaging means, such as cans, bottles, or similar containers, by treating the packaging means interior surface with electron radiation from at least one treatment head 15, wherein the treatment head for the treatment is introduced into the respective packaging means 2, or into the packaging means interior through a packaging means opening 2.1.

One feature or aspect of an embodiment is believed at the time of the filing of this patent application to possibly reside broadly in a method for sterilizing packaging means, such as, for example, cans, bottles or similar containers, by treating the inside surface of the packaging means with electron radiation from at least one treatment head 15, wherein the treatment head for the treatment is placed in the respective packaging means 2 or in the interior of the packaging means through a packaging means opening 2.1.

Another feature or aspect of an embodiment is believed at the time of the filing of this patent application to possibly reside broadly in the method, comprising the use of at least one treatment head 15, which is realized with regard to its radiation characteristic such that at least the entire inside surface of the packaging means located in a direction of radiation or in an angular region of radiation is impinged upon with identical or substantially identical radiated power.

Yet another feature or aspect of an embodiment is believed at the time of the filing of this patent application to possibly reside broadly in the method, comprising the use of at least one treatment head 15, which is realized with regard to its radiation characteristic such that the entire inside surface of the treated packaging means is impinged upon with identical or substantially identical radiation intensity.

Still another feature or aspect of an embodiment is believed at the time of the filing of this patent application to possibly reside broadly in the method, comprising at least one rod-shaped treatment head 15 for transmitting radial or substantially radial and/or axial or substantially axial electron radiation.

A further feature or aspect of an embodiment is believed at the time of the filing of this patent application to possibly reside broadly in the method, wherein the respective packaging means 2 and the at least one treatment head 15 placed into the interior of the packaging means are moved relative to one another during the electron beam treatment, for example in a translational manner and/or in a rotational manner.

Another feature or aspect of an embodiment is believed at the time of the filing of this patent application to possibly reside broadly in the method, wherein the placing of the at least one treatment head 15 in the interior of the packaging means is effected by means of an advancing movement of the packaging means 2 relative to the at least one treatment head 15.

Yet another feature or aspect of an embodiment is believed at the time of the filing of this patent application to possibly reside broadly in the method, wherein the placing of the at least one treatment head 15 in the interior of the packaging means is effected by means of raising the packaging means 2 in a vertical direction or a substantially vertical direction.

Still another feature or aspect of an embodiment is believed at the time of the filing of this patent application to possibly reside broadly in the method, wherein the placing of the at least one treatment head 15 in the interior of the packaging means is effected by means of an advancing movement of the packaging means 2 in a horizontal or substantially horizontal direction.

A further feature or aspect of an embodiment is believed at the time of the filing of this patent application to possibly reside broadly in the method, wherein prior to the advancing movement, the packaging means 2 is moved and/or pivoted out of an initial position into a position in which the opening 2.1 of the packaging means 2 is situated opposite the at least one treatment head 15 in the axis of the advancing movement.

Another feature or aspect of an embodiment is believed at the time of the filing of this patent application to possibly reside broadly in the method, comprising the use of a sterilizer 3, which, on a conveyor, for example in the form of a rotor 14 driven in a rotating manner about a vertical or substantially vertical machine axis MA1, has a plurality of treatment stations 13 each with at least one treatment head 15 and one container support 16 associated with each treatment head 15.

Yet another feature or aspect of an embodiment is believed at the time of the filing of this patent application to possibly reside broadly in the method, wherein the packaging means 2 are also treated on their outside surface for sterilization or disinfection with the electron radiation of at least one treatment head 21.

Still another feature or aspect of an embodiment is believed at the time of the filing of this patent application to possibly reside broadly in the method, wherein after the sterilizing, the packaging means 2 are filled with a liquid product and closed.

A further feature or aspect of an embodiment is believed at the time of the filing of this patent application to possibly reside broadly in the method, wherein the closing of the filled packaging means is effected by using closures 30, which, prior to being fitted onto the respective packaging means 2, are treated by way of the electron sterilization or electron disinfection of at least their inside surface with the electron radiation of at least one treatment head 35.

One feature or aspect of an embodiment is believed at the time of the filing of this patent application to possibly reside broadly in the method, wherein the closing of the packaging means 2 is effected using at least one closing tool 27 with at least one closing head or tool head 28, which is realized for receiving in each case at least one closure 30 and for applying the closure 30 to the packaging means 2, and in that the respective closure 30 with the closing head or tool head 28 is moved past the at least one treatment head 35 for the electron sterilization or electron disinfection.

Another feature or aspect of an embodiment is believed at the time of the filing of this patent application to possibly reside broadly in the method, comprising the use of a closing machine 5, which, on a rotating conveyor, for example on a rotor 26 that is driven in a rotating manner about a vertical or substantially vertical machine axis MA2, has at least one closing tool 27 with closing head or tool head 28, and in that the at least one treatment head 35, not entrained by the conveyor, is provided on a transport section between a closure removal position 31, at which the respective closure 30 is removed by the closing head or tool head 28, and a position at which a fitting of the closure onto the respective packaging means 2 is effected.

Yet another feature or aspect of an embodiment is believed at the time of the filing of this patent application to possibly reside broadly in the method, wherein the at least one treatment head 15, 21, 35, 38 is activated for the delivery of the electron radiation during the treatment of the respective packaging means.

Still another feature or aspect of an embodiment is believed at the time of the filing of this patent application to possibly reside broadly in the method, wherein the packaging means are produced using plastics material, for example bottles, cans or similar containers made of plastics material, e.g. PET.

A further feature or aspect of an embodiment is believed at the time of the filing of this patent application to possibly reside broadly in the method, wherein the sterilizing, filling and closing of the packaging means 2 is effected in a sterile or clean room 7.

Another feature or aspect of an embodiment is believed at the time of the filing of this patent application to possibly reside broadly in the method, wherein the packaging means 2, in one possible embodiment the interior of the packaging means is treated additionally with a fluid treatment medium, for example $CO_2$, $N_2$, $H_2O_2$ and/or air.

Yet another feature or aspect of an embodiment is believed at the time of the filing of this patent application to possibly reside broadly in a device for treating packaging means, in one possible embodiment packaging means 2 realized as hollow bodies, such as, for example, cans, bottles or similar containers, said device having at least one treatment station 13 with at least one treatment head 15 with an electron beam source for electron sterilization or electron disinfection, wherein for the electron sterilization or electron disinfection of the respective interior of the packaging means, the at least one treatment station 13 is realized for placing the at least one treatment head 15 in the packaging means 2 during the treatment and for removing the at least one treatment head 15 out of the packaging means 2 after the treatment.

Still another feature or aspect of an embodiment is believed at the time of the filing of this patent application to possibly reside broadly in the device, wherein a plurality of treatment stations 13, in each case having at least one treatment head 15, are provided at a rotatingly driveable transport element, for example at a rotor 14 that is driveable in a rotating manner about a vertical or substantially vertical machine axis MA1.

A further feature or aspect of an embodiment is believed at the time of the filing of this patent application to possibly reside broadly in the device, wherein each treatment station 13 has associated therewith at least one packaging means support 16, and in that the treatment head 15 and the packaging means support 16 are moveable in a controlled manner one relative to the other for an advancing movement.

Another feature or aspect of an embodiment is believed at the time of the filing of this patent application to possibly reside broadly in the device, wherein the at least one treatment head 15 and the associated packaging means support 16 are moveable in a controlled manner one relative to the other in the horizontal or substantially horizontal axial direction, in one possible embodiment radially to the axis of rotation of the rotor 14, and/or in the vertical or substantially vertical axial direction.

Yet another feature or aspect of an embodiment is believed at the time of the filing of this patent application to possibly reside broadly in the device, wherein the packaging means support 16 is moveable in a controlled manner for placing the at least one treatment head 15 in the interior of the packaging means and for removing the treatment head 15 out of the interior of the packaging means.

Still another feature or aspect of an embodiment is believed at the time of the filing of this patent application to possibly reside broadly in the device, wherein the packaging means support 16 is moveable or pivotable with the respective packaging means 2 out of an initial position into a ready position in which the packaging means 2 is oriented with the axis of its packaging means opening 2.1 parallel or substantially parallel to the axis of the advancing movement between treatment head 15 and container support 16.

A further feature or aspect of an embodiment is believed at the time of the filing of this patent application to possibly reside broadly in the device, wherein, for the electron sterilization or electron disinfection of the packaging means 2 on its outside surface, at least one treatment head 21 is provided on a path of movement of the treatment stations 13 moved by way of the transport element 14.

One feature or aspect of an embodiment is believed at the time of the filing of this patent application to possibly reside broadly in a device for treating packaging means in the form of closures 30 for cans, bottles or similar containers 2, said device having at least one treatment station with at least one treatment head 35 with an electron beam source for electron sterilization or electron disinfection, wherein the at least one treatment head 35 is provided for the electron sterilization or electron disinfection of at least the respective inside of the closure directly prior to the closing of a container 2.

Another feature or aspect of an embodiment is believed at the time of the filing of this patent application to possibly reside broadly in the device, wherein the at least one treatment head 35 is provided at or in a closing machine 5.

Yet another feature or aspect of an embodiment is believed at the time of the filing of this patent application to possibly reside broadly in the device, comprising at least one closing tool 27 with a closing head or tool head 28 for receiving the respective closure 30 at a receiving position 31 and for fitting and securing the closure 30 to a packaging means 2, wherein at least one treatment head 35 transmitting electron or beta radiation is located on a path of movement on which the closing head or tool head 28 is moved between the receiving position 31 and the mounting of the closure onto the respective packing means 2.

Still another feature or aspect of an embodiment is believed at the time of the filing of this patent application to possibly reside broadly in the device, wherein the at least one treatment station 13 is realized for a relative movement, in one possible embodiment for a translational and/or rotational relative movement between the respective packaging means 2 and the at least one treatment head 15, 21, 35, 38 during the treatment.

A further feature or aspect of an embodiment is believed at the time of the filing of this patent application to possibly reside broadly in the device, wherein each treatment head 15, 21, 35, 38 has associated therewith an independent electron beam source.

Another feature or aspect of an embodiment is believed at the time of the filing of this patent application to possibly reside broadly in the device, wherein one electron beam source is provided for the treatment heads 15, 21, 35, 38 in common or for a group of treatment heads 15, 21, 35, 38.

Yet another feature or aspect of an embodiment is believed at the time of the filing of this patent application to possibly reside broadly in the device, wherein the at least one treatment head 15, 21, 35, 38 is realized for the delivery of electron or beta radiation at an energy in the order of one hundred kiloelectron volts and one hundred fifty kiloelectron volts.

Still another feature or aspect of an embodiment is believed at the time of the filing of this patent application to possibly reside broadly in the device, wherein the at least one treatment head 15, 21, 35, 38 is realized for a treatment of the packaging means 2 at a radiation dose in excess of five kilograys, in one possible embodiment at a dose within the range of approximately nine kilograys to sixty kilograys.

A further feature or aspect of an embodiment is believed at the time of the filing of this patent application to possibly reside broadly in the device, wherein the output or radiation intensity of the at least one treatment head 15, 21, 35, 38 is controllable or regulatable as a function of the output of the device (number of packaging means treated per unit time).

Another feature or aspect of an embodiment is believed at the time of the filing of this patent application to possibly reside broadly in the device, wherein said device is a component of an installation 1 for filling and closing the packaging means 2, wherein the installation, in a sterile or clean room 7, has at least one device or machine for filling the packaging means 2 as well as at least one item of equipment or device 5 for closing the packaging means 2 by way of closures 30.

Yet another feature or aspect of an embodiment is believed at the time of the filing of this patent application to possibly reside broadly in the device, wherein said device or the at least one treatment head 15 is provided directly in or on a machine 4 for packing or filling products into packaging means 2.

Still another feature or aspect of an embodiment is believed at the time of the filing of this patent application to possibly reside broadly in the device, wherein the at least one treatment head 15, 21, 35, 38 and/or the electron beam source forming said treatment head 15, 21, 35, 38 or associated with said treatment head 15, 21, 35, 38 is provided with a cooling means, for example with a cooling means using a gaseous and/or vaporous or liquid cooling medium.

A further feature or aspect of an embodiment is believed at the time of the filing of this patent application to possibly reside broadly in the device, wherein the at least one treatment head 15 is realized for rinsing or treating the respective packaging means 2 and/or interior of the packaging means with an inert gaseous and/or vaporous medium, e.g. with $CO_2$, $N_2$, $H_2O_2$ and/or sterile air.

One feature or aspect of an embodiment is believed at the time of the filing of this patent application to possibly reside broadly in the device, wherein the at least one treatment head 15 is realized for removing or aspirating gaseous and/or vaporous constituents from the interior of the packaging means.

Another feature or aspect of an embodiment is believed at the time of the filing of this patent application to possibly reside broadly in an installation for filling and closing packaging means 2, such as, for example, cans, bottles or similar containers, said installation having a packing or filling machine 4 located in a sterile or clean room 7 and a closing machine 5 located in the sterile or clean room 7, wherein, in addition, a device for the electron beam sterilization or electron beam disinfection of the packaging means 2 or of the respective interior of the packaging means prior to it being conveyed further to the packing or filling machine 4 is provided in the sterile or clean room 7.

Yet another feature or aspect of an embodiment is believed at the time of the filing of this patent application to possibly reside broadly in the installation, wherein at least one treatment head 35 for the electron sterilization or electron disinfection of the closures 30 is provided at and/or in the closing machine 5.

Still another feature or aspect of an embodiment is believed at the time of the filing of this patent application to possibly reside broadly in the installation, wherein the device for the electron beam sterilization or electron beam disinfection of the packaging means 2 or of the respective interior of the packaging means or of the closures is realized according to the present application.

A further feature or aspect of an embodiment is believed at the time of the filing of this patent application to possibly reside broadly in a method of operating a beverage bottling plant, said method comprising the steps of: feeding plastic beverage bottles into a beverage bottling plant; moving plastic beverage bottles into a rotary beverage bottle treating machine of said beverage bottling plant; moving plastic beverage bottles in a circular path in said rotary beverage bottle treating machine; generating at least one beam with a beam generator arrangement; inserting treatment heads of said rotary beverage bottle treating machine through beverage bottle mouths and into plastic beverage bottles; conducting at least one beam from said beam generator arrangement to said treatment heads with a conducting arrangement; treating the insides of plastic beverage bottles with at least one beam from said beam generator arrangement in said rotary beverage bottle treating machine and substantially simultaneously minimizing deformation of plastic beverage bottles during treating by said step of treating with at least one beam; moving plastic beverage bottles from said rotary beverage bottle treating machine to a rotary beverage bottle filling machine of said beverage bottling plant; moving plastic beverage bottles in a circular path in said rotary beverage bottle filling machine; filling treated plastic beverage bottles with a liquid beverage material in said rotary beverage bottle filling machine; moving filled, plastic beverage bottles from said rotary beverage bottle filling machine to a rotary beverage bottle closing machine of said beverage bottling plant; moving plastic beverage bottles in a circular path in said rotary beverage bottle closing machine; conducting at least one beam from said beam generator arrangement to treatment heads of said rotary beverage bottle closing machine with said conducting arrangement; treating beverage bottle screw caps with at least one beam from said beam generator arrangement; closing filled, plastic beverage bottles with treated beverage bottle screw caps in said rotary beverage bottle closing machine; moving closed, filled, plastic beverage bottles from said rotary beverage bottle closing machine of said beverage bottling plant; and feeding closed, filled, plastic beverage bottles from said beverage bottling plant.

The components disclosed in the various publications, disclosed or incorporated by reference herein, may possibly be used in possible embodiments of the present invention, as well as equivalents thereof.

The purpose of the statements about the technical field is generally to enable the Patent and Trademark Office and the public to determine quickly, from a cursory inspection, the nature of this patent application. The description of the technical field is believed, at the time of the filing of this patent application, to adequately describe the technical field of this patent application. However, the description of the technical field may not be completely applicable to the claims as originally filed in this patent application, as amended during prosecution of this patent application, and as ultimately allowed in any patent issuing from this patent application. Therefore, any statements made relating to the technical field are not intended to limit the claims in any manner and should not be interpreted as limiting the claims in any manner.

The appended drawings in their entirety, including all dimensions, proportions and/or shapes in at least one embodiment of the invention, are accurate and are hereby included by reference into this specification.

The background information is believed, at the time of the filing of this patent application, to adequately provide background information for this patent application. However, the background information may not be completely applicable to the claims as originally filed in this patent application, as amended during prosecution of this patent application, and as ultimately allowed in any patent issuing from this patent application. Therefore, any statements made relating to the background information are not intended to limit the claims in any manner and should not be interpreted as limiting the claims in any manner.

All, or substantially all, of the components and methods of the various embodiments may be used with at least one embodiment or all of the embodiments, if more than one embodiment is described herein.

The purpose of the statements about the object or objects is generally to enable the Patent and Trademark Office and the public to determine quickly, from a cursory inspection, the nature of this patent application. The description of the object or objects is believed, at the time of the filing of this patent application, to adequately describe the object or objects of this patent application. However, the description of the object or objects may not be completely applicable to the claims as originally filed in this patent application, as amended during prosecution of this patent application, and as ultimately allowed in any patent issuing from this patent application. Therefore, any statements made relating to the object or objects are not intended to limit the claims in any manner and should not be interpreted as limiting the claims in any manner.

All of the patents, patent applications and publications recited herein, and in the Declaration attached hereto, are hereby incorporated by reference as if set forth in their entirety herein except for the exceptions indicated herein.

The summary is believed, at the time of the filing of this patent application, to adequately summarize this patent application. However, portions or all of the information contained in the summary may not be completely applicable to the claims as originally filed in this patent application, as amended during prosecution of this patent application, and as ultimately allowed in any patent issuing from this patent application. Therefore, any statements made relating to the summary are not intended to limit the claims in any manner and should not be interpreted as limiting the claims in any manner.

It will be understood that the examples of patents, published patent applications, and other documents which are included in this application and which are referred to in paragraphs which state "Some examples of . . . which may possibly be used in at least one possible embodiment of the present application . . . " may possibly not be used or useable in any one or more embodiments of the application.

The sentence immediately above relates to patents, published patent applications and other documents either incorporated by reference or not incorporated by reference.

The following patents, patent applications or patent publications, are hereby incorporated by reference as if set forth in their entirety herein except for the exceptions indicated herein: DE 198 82 252 T1, having the following English translation of the German title "TECHNIQUE FOR INTE- RIOR ELECTRON STERILIZATION OF AN OPEN MOUTHED CONTAINER," published on May 18, 2000.

All of the patents, patent applications or patent publications, except for the exceptions indicated herein, which were cited in the International Search Report dated Apr. 8, 2009, and/or cited elsewhere are hereby incorporated by reference as if set forth in their entirety herein, as follows: US 2007/0283667, having the title "METHOD OF STERILIZING PACKAGES," published on Dec. 13, 2007; WO 2007/095205, having the title "ELECTRON BEAM EMITTER," published on Aug. 23, 2007; EP 1 561 722, having the following English translation of the German title "BEVERAGE BOTTLING PLANT FOR FILLING BOTTLES WITH A LIQUID BEVERAGE MATERIAL AND AN ASEPTIC BOTTLING SYSTEM FOR THE ASEPTIC BOTTLING FOR A LIQUID MATERIAL," published on Aug. 10, 2005; WO 2005/108278, having the title "APPARATUSES AND METHODS FOR STERILISING AND FILLING COMPONENTS OF PACKAGING UNITS, PARTICULARLY BOTTLES AND/OR CAPS," published on Nov. 17, 2005; and GB 2,384,778, having the title "IRRADIATING BOTTLE FILLING MACHINE," published on Sep. 11, 1945.

All of the patents, patent applications or patent publications, except for the exceptions indicated herein, which were cited in the German Office Action dated Oct. 24, 2008, and/or cited elsewhere are hereby incorporated by reference as if set forth in their entirety herein, as follows: WO 2007/145561, having the title "METHOD OF STERILIZING PACKAGES," published on Dec. 21, 2007; US 2007/0237672, having the title "Apparatuses and Methods for Sterilising and Filling Components of Packaging Units Particularly Bottles and/or Caps," published on Oct. 11, 2007; EP 17 36 174, having the title "Electron beam sterilizer," published on Dec. 27, 2006; FR 28 65 135, having the following French title "INSTALLATION DE STERILISATION D'ARTICLES PAR BOMBARDEMENT ELECTRONIQUE," published on Jul. 22, 2005; WO 2008/073015, having the title "METHOD AND DEVICE FOR IRRADIATING OBJECTS," published on Jun. 19, 2008; and WO 2008/070956, having the title "ELECTRON BEAM STERILIZING AND CRYSTALLIZING OF PREFORMS," published on Jun. 19, 2008.

Some examples of methods and apparatuses for closing bottles and containers and their components that may possibly be utilized or possibly adapted for use in at least one possible embodiment of the present application may possibly be found in the following U.S. Pat. No. 5,398,485 issued to Osifchin on Mar. 21, 1995; U.S. Pat. No. 5,402,623 issued to Ahlers on Apr. 4, 1995; U.S. Pat. No. 5,419,094 issued to Vander Bush, Jr. et al. on May 30, 1995; U.S. Pat. No. 5,425,402 issued to Pringle on Jun. 20, 1995; U.S. Pat. No. 5,447,246 issued to Finke on Sep. 5, 1995; and U.S. Pat. No. 5,449,080 issued to Finke on Sep. 12, 1995.

Some examples of filling machines that utilize electronic control devices to control various portions of a filling or bottling process and that may possibly be utilized or possibly adapted for use in at least one possible embodiment of the present application may possibly be found in the following U.S. Pat. No. 4,821,921 issued to Cartwright et al. on Apr. 18, 1989; U.S. Pat. No. 5,056,511 issued to Ronge on Oct. 15, 1991; U.S. Pat. No. 5,273,082 issued to Paasche et al. on Dec. 28, 1993; and U.S. Pat. No. 5,301,488 issued to Ruhl et al. on Apr. 12, 1994.

Some examples of bottling systems which may possibly be utilized or adapted for use in at least one possible embodiment may possibly be found in the following U.S. Pat. No. 6,684,602, entitled "Compact bottling machine;" U.S. Pat. No. 6,470,922, entitled "Bottling plant for bottling carbonated beverages;" U.S. Pat. No. 6,390,150, entitled "Drive for bottling machine;" U.S. Pat. No. 6,374,575, entitled "Bottling plant and method of operating a bottling plant;" U.S. Pat. No. 6,192,946, entitled "Bottling system;" U.S. Pat. No. 6,185,910, entitled "Method and an apparatus for high-purity bottling of beverages;" U.S. Pat. No. 6,058,985, entitled "Bottling machine with a set-up table and a set-up table for a bottling machine and a set-up table for a bottle handling machine;" U.S. Pat. No. 5,996,322, entitled "In-line bottling plant;" U.S. Pat. No. 5,896,899, entitled "Method and an apparatus for sterile bottling of beverages;" U.S. Pat. No. 5,848,515, entitled "Continuous-cycle sterile bottling plant;" U.S. Pat. No. 5,634,500, entitled "Method for bottling a liquid in bottles or similar containers;" and U.S. Pat. No. 5,425,402, entitled "Bottling system with mass filling and capping arrays."

Some examples of apparatuses for treating and/or sterilizing with electron beams, which may possibly be utilized or adapted for use with at least one possible embodiment of the present application, may possibly be found in the following U.S. Pat. No. 7,626,186, having the title "Mobile electron beam radiation sterilizing apparatus," published on Dec. 1, 2009; U.S. Pat. No. 7,417,239, having the title "Method and device for election beam irradiation," published on Aug. 26, 2008; U.S. Pat. No. 7,365,343, having the title "Apparatus and process for filling a medicament into a container," published on Apr. 29, 2008; and U.S. Pat. No. 7,348,578, having the title "Device and method for electron beam irradiation," published on Mar. 25, 2008.

Some examples of apparatuses and/or methods for guiding or focusing electron beams, which may possibly be utilized or adapted for use in at least one possible embodiment of the present application, may possibly be found in the following U.S. Pat. No. 6,844,557, having the title "System for, and method of, irradiating opposite sides of an article," published on Jan. 18, 2005; U.S. Pat. No. 7,759,653, having the title "Electron beam apparatus," published on Jul. 20, 2010; U.S. Pat. No. 7,718,981, having the title "Composite charged-particle beam system," published on May 18, 2010; U.S. Pat. No. 7,737,412, having the title "Electron microscope phase enhancement," published on Jun. 15, 2010; and U.S. Pat. No. 7,705,301, having the title "Electron beam apparatus to collect side-view and/or plane-view image with in-lens sectional detector," published on Apr. 27, 2010.

The patents, patent applications, and patent publications listed above in the preceding paragraphs are herein incorporated by reference as if set forth in their entirety except for the exceptions indicated herein. The purpose of incorporating U.S. patents, Foreign patents, publications, etc. is solely to provide additional information relating to technical features of one or more embodiments, which information may not be completely disclosed in the wording in the pages of this application. However, words relating to the opinions and judgments of the author and not directly relating to the technical details of the description of the embodiments therein are not incorporated by reference. The words all, always, absolutely, consistently, preferably, guarantee, particularly, constantly, ensure, necessarily, immediately, endlessly, avoid, exactly, continually, expediently, ideal, need, must, only, perpetual, precise, perfect, require, requisite, simultaneous, total, unavoidable, and unnecessary, or words substantially equivalent to the above-mentioned words in this sentence, when not used to describe technical features of one or more embodiments of the patents, patent applications, and patent publications, are not considered to be incorporated by reference herein.

The corresponding foreign and international patent publication applications, namely, Federal Republic of Germany Patent Application No. 10 2008 007 428.4, filed on Feb. 1, 2008, having inventors Alfred DRENGUIS and Volker TILL, and DE-OS 10 2008 007 428.4 and DE-PS 10 2008 007 428.4, and International Application No. PCT/EP2009/000399, filed on Jan. 23, 2009, having WIPO Publication No. WO2009/095182 and inventors Alfred DRENGUIS and Volker TILL, are hereby incorporated by reference as if set forth in their entirety herein, except for the exceptions indicated herein, for the purpose of correcting and explaining any possible misinterpretations of the English translation thereof. In addition, the published equivalents of the above corresponding foreign and international patent publication applications, and other equivalents or corresponding applications, if any, in corresponding cases in the Federal Republic of Germany and elsewhere, and the references and documents cited in any of the documents cited herein, such as the patents, patent applications and publications, except for the exceptions indicated herein, are hereby incorporated by reference as if set forth in their entirety herein.

The purpose of incorporating the corresponding foreign equivalent patent application(s), that is, PCT/EP2009/000399 and German Patent Application 10 2008 007 428.4, is solely for the purpose of providing a basis of correction of any wording in the pages of the present application, which may have been mistranslated or misinterpreted by the translator. However, words relating to opinions and judgments of the author and not directly relating to the technical details of the description of the embodiments therein are not to be incorporated by reference. The words all, always, absolutely, consistently, preferably, guarantee, particularly, constantly, ensure, necessarily, immediately, endlessly, avoid, exactly, continually, expediently, ideal, need, must, only, perpetual, precise, perfect, require, requisite, simultaneous, total, unavoidable, and unnecessary, or words substantially equivalent to the above-mentioned word in this sentence, when not used to describe technical features of one or more embodiments of the patents, patent applications, and patent publications, are not generally considered to be incorporated by reference herein.

Statements made in the original foreign patent applications PCT/EP2009/000399 and DE 10 2008 007 428.4 from which this patent application claims priority which do not have to do with the correction of the translation in this patent application are not to be included in this patent application in the incorporation by reference.

Any statements about admissions of prior art in the original foreign patent applications PCT/EP2009/000399 and DE 10 2008 007 428.4 are not to be included in this patent application in the incorporation by reference, since the laws relating to prior art in non-U.S. Patent Offices and courts may be substantially different from the Patent Laws of the United States.

All of the references and documents cited in any of the documents cited herein, except for the exceptions indicated herein, are hereby incorporated by reference as if set forth in their entirety herein. All of the documents cited herein, referred to in the immediately preceding sentence, include all of the patents, patent applications and publications cited anywhere in the present application.

The description of the embodiment or embodiments is believed, at the time of the filing of this patent application, to adequately describe the embodiment or embodiments of this patent application. However, portions of the description of the embodiment or embodiments may not be completely applicable to the claims as originally filed in this patent application, as amended during prosecution of this patent application, and as ultimately allowed in any patent issuing from this patent application. Therefore, any statements made relating to the embodiment or embodiments are not intended to limit the claims in any manner and should not be interpreted as limiting the claims in any manner.

The details in the patents, patent applications and publications may be considered to be incorporable, at applicant's option, into the claims during prosecution as further limitations in the claims to patentably distinguish any amended claims from any applied prior art.

The purpose of the title of this patent application is generally to enable the Patent and Trademark Office and the public to determine quickly, from a cursory inspection, the nature of this patent application. The title is believed, at the time of the filing of this patent application, to adequately reflect the general nature of this patent application. However, the title may not be completely applicable to the technical field, the object or objects, the summary, the description of the embodiment or embodiments, and the claims as originally filed in this patent application, as amended during prosecution of this patent application, and as ultimately allowed in any patent issuing from this patent application. Therefore, the title is not intended to limit the claims in any manner and should not be interpreted as limiting the claims in any manner.

The abstract of the disclosure is submitted herewith as required by 37 C.F.R. §1.72(b). As stated in 37 C.F.R. §1.72(b):

A brief abstract of the technical disclosure in the specification must commence on a separate sheet, preferably following the claims, under the heading "Abstract of the Disclosure." The purpose of the abstract is to enable the Patent and Trademark Office and the public generally to determine quickly from a cursory inspection the nature and gist of the technical disclosure. The abstract shall not be used for interpreting the scope of the claims.

Therefore, any statements made relating to the abstract are not intended to limit the claims in any manner and should not be interpreted as limiting the claims in any manner.

The embodiments of the invention described herein above in the context of the preferred embodiments are not to be taken as limiting the embodiments of the invention to all of the provided details thereof, since modifications and variations thereof may be made without departing from the spirit and scope of the embodiments of the invention.

AT LEAST PARTIAL NOMENCLATURE

1 Installation
2 Bottle
2.1 Bottle mouth
2.2 Neck flange
3 Sterilizer
4 Filling machine
5 Closing machine
6 Enclosure
7 Sterile or clean room
8, 9 Staff lock
10 Conveyor
11 Entry lock
12 Transport star
13 Treatment station
14 Rotor
15 Treatment head with electron beam source
15.1 Electron beam outlet window
16 Container support
17 Pivotal axis 18 Carriage
19 Guide means
20 Linkage
21 Radiation head with electron beam source
22 Transport star
23 Rotor
24 Transport star
25 Closing station
26 Rotor
27 Closing tool
28 Closing or tool head
29 Container support
30 Closure or cover
31 Closure removal position
32 Closure supply
33 Conveyor
34 Exit lock
35 Treatment head with electron beam source
35.1 Electron beam
36 Channel
37 Inlet for sterile air
38 Treatment head
A Direction of rotation of the rotor 14
B Direction of rotation of the container support 16
C Movement of the carriage 18
D Direction of rotation of the rotor 23
E Direction of rotation of the rotor 26
MA1, MA2 Machine axis

What is claimed is:

1. A method for sterilizing bottles that comprise a mouth portion, a neck portion, a body portion, and a shoulder portion that connects said neck portion to said body portion and is transversely oriented with respect to said neck portion and said body portion, said method comprising the steps of:
   relatively moving a bottle and a treatment member with respect to one another, and thereby disposing solely at least portion of said treatment member inside said bottle via mouth said mouth portion,
   which said mouth portion comprises the sole opening into and out of said bottle, and which said treatment member is configured to emit electron radiation and is elongated;
   treating, using solely said treatment member, the entire inside surface of each portion of the bottle by uniformly impinging the entire inside surface of the bottle with identical or essentially identical radiation power and intensity, radiated from said treatment member to the inside surface;
   relatively moving said bottle and said treatment member again with respect to one another, and thereby disposing said treatment member outside of said bottle; and
   wherein said treatment member comprises a longitudinal axis, elongated side surfaces, and an end surface, and said step of treating comprises:
      radiating electron radiation substantially radially, with respect to said longitudinal axis, from said side surfaces; and
      radiating electron radiation substantially axially, with respect to said longitudinal axis, from said end surface of said treatment member.

2. The method for sterilizing bottles according to claim 1, wherein:
   said sterilization device comprises:
      a rotor having a vertical axis of rotation;
      a plurality of bottle supports disposed on and about the periphery of said rotor; and
      a plurality of said treatment members disposed on and about the periphery of said rotor, one treatment member for each of said bottle supports;
   said method further comprises treating the outside surface of said bottle with electron radiation from at least one additional electron radiation treatment device separate from said rotor; and
   said steps of relatively moving said bottle and said treatment member with respect to one another comprise moving the bottle in a horizontal direction or an essentially horizontal direction with respect to said vertical axis of rotation.

3. The method for sterilizing bottles according to claim 2, wherein said step of radiating electron radiation radially comprises radiating electron radiation at a uniform radiation dose within a range of approximately 9-60 kGy.

4. The method for sterilizing bottles according to claim 3, wherein:
   said method further comprises relatively moving said bottle and said treatment member with respect to one another until said treatment member is disposed at a treatment position inside said bottle in which said treatment member extends over most of the height of said bottle; and
   said method further comprises activating said treatment member only upon said treatment member being disposed in said treatment position.

5. A sterilization arrangement for sterilizing bottles that comprise a mouth portion, a neck portion, a body portion, and a shoulder portion that connects said neck portion to said body portion and is transversely oriented with respect to said neck portion and said body portion, said sterilization arrangement comprising:
   at least one treatment member, each being elongated and being configured and disposed to radiate electron radiation to the entire inside surface of a bottle to uniformly impinge the entire inside surface of the bottle with identical or essentially identical radiation power;
   at least one bottle support configured to support a bottle;
   said at least one treatment member and said at least one bottle support being configured to be moved relative to one another to thereby dispose at least portion of said treatment member inside the bottle solely via the mouth portion, and to thereby subsequently dispose said treatment member outside of the bottle;
   said at least one treatment member comprises a longitudinal axis, elongated side surfaces, and an end surface; and
   said at least one treatment member is configured to radiate electron radiation substantially radially, with respect to said longitudinal axis, from said side surfaces, and configured to radiate electron radiation substantially axially, with respect to said longitudinal axis, from said end surface.

6. The sterilization arrangement according to claim 5, wherein:
   said sterilization arrangement comprises a rotor having a vertical axis of rotation;
   said at least one bottle support comprises a plurality of bottle supports disposed on and about the periphery of said rotor;
   said at least one treatment member comprises a plurality of treatment members disposed on and about the periphery of said rotor, one treatment member for each of said bottle supports;
   said sterilization arrangement further comprises at least one additional electron radiation treatment device separate from said rotor and configured to treat the outside surfaces of said bottles with electron radiation; and each of said plurality of bottle supports is configured to move a bottle supported thereby in a horizontal direction or an essentially horizontal direction with respect to said vertical axis of rotation of said rotor.

7. The sterilization device according to claim 6, wherein: each of said treatment members is configured to radiate electron radiation at a uniform radiation dose within a range of approximately 9-60 kGy.

8. The sterilization device according to claim 7, wherein:

said at least one treatment member and said at least one bottle support are configured to be moved relative to one another until said treatment member is disposed at a treatment position inside said bottle in which said treatment member extends over most of the height of said bottle; and said at least one treatment member is configured to be activated only upon said at least one treatment member being disposed in said treatment position.

9. The sterilization device according to claim 8 in combination with a bottle-handling plant, the combination comprising:

a filling machine for filling bottles;

a closing machine for closing filled bottles; and a clean room in which said filling machine, said closing machine, and said sterilization device are located.

* * * * *